(12) United States Patent
Shawcross et al.

(10) Patent No.: US 9,096,943 B2
(45) Date of Patent: Aug. 4, 2015

(54) METAL TREATMENT

(75) Inventors: James Timothy Shawcross, Charlbury (GB); David Richard Lewis, Abingdon (GB); Andrew Derek Turner, Abingdon (GB)

(73) Assignee: Accentus Medical Limited, Didcot (GB)

( * ) Notice: Subject to any disclaimer, the term of this patent is extended or adjusted under 35 U.S.C. 154(b) by 377 days.

(21) Appl. No.: 13/262,350

(22) PCT Filed: Mar. 29, 2010

(86) PCT No.: PCT/GB2010/050531
§ 371 (c)(1),
(2), (4) Date: Sep. 30, 2011

(87) PCT Pub. No.: WO2010/112908
PCT Pub. Date: Oct. 7, 2010

(65) Prior Publication Data
US 2012/0018308 A1    Jan. 26, 2012

(30) Foreign Application Priority Data

Mar. 30, 2009  (GB) .................................. 0905354.7
Nov. 20, 2009  (GB) .................................. 0920314.2

(51) Int. Cl.
*C25D 11/26*    (2006.01)
*A61L 31/02*    (2006.01)
(Continued)

(52) U.S. Cl.
CPC ............... *C25D 11/26* (2013.01); *A61L 31/022* (2013.01); *A61L 31/088* (2013.01); *A61L 31/16* (2013.01); *A61L 2300/104* (2013.01); *A61L 2300/404* (2013.01)

(58) Field of Classification Search
CPC .......................................................... C25D 11/26
USPC ......................................... 205/106, 200, 220
See application file for complete search history.

(56) References Cited

U.S. PATENT DOCUMENTS 4,822,458 A  *  4/1989  Ogden .......................... 205/106
5,160,599 A  *  11/1992  Kobayashi et al. ........... 205/106
(Continued)

FOREIGN PATENT DOCUMENTS

WO    WO 2005/087982 A1    9/2005
WO    WO 2009/044203 A1    4/2009

OTHER PUBLICATIONS

F. A. Lowenheim, Electroplating, McGraw-Hill Book Company, New York, 1978, pp. 12-24.*

(Continued)

*Primary Examiner* — Bryan D. Ripa
(74) *Attorney, Agent, or Firm* — Christensen O'Connor Johnson Kindness PLLC

(57) ABSTRACT

Metal objects are treated by anodising (P, SE) the metal object in contact with an acidic solution, and then subjecting the anodised metal object to a reversed voltage (VR). The anodising is performed in two stages, firstly to passivate (P) with the formation of a surface layer, and secondly to form pits in this surface layer (SE). The second stage (SE) of anodising is performed at a lower voltage than the first stage (P). After the reversed voltage step (VR) the metal object is then contacted with a biocidal metal-containing solution. Biocidal metal is absorbed into the surface of the metal object, resulting in improved biocidal properties. The lower voltage of the second stage anodising (SE) results in reduced processing time.

12 Claims, 2 Drawing Sheets

(51) Int. Cl.
*A61L 31/08* (2006.01)
*A61L 31/16* (2006.01)

(56) References Cited

U.S. PATENT DOCUMENTS

| | | | | |
|---|---|---|---|---|
| 5,340,605 | A | * | 8/1994 | Silver et al. ................ 427/126.3 |
| 5,500,106 | A | * | 3/1996 | Goldberg ...................... 205/166 |
| 5,919,561 | A | * | 7/1999 | Fuchs et al. .................. 428/336 |
| 6,267,782 | B1 | * | 7/2001 | Ogle et al. ..................... 623/1.1 |
| 7,727,372 | B2 | * | 6/2010 | Liu et al. ....................... 205/106 |
| 2007/0181221 | A1 | * | 8/2007 | Pickford et al. .............. 148/239 |
| 2007/0187253 | A1 | * | 8/2007 | Gilbert et al. .................. 205/80 |

OTHER PUBLICATIONS

PCT Interrnational Search Report and Written Opinion for International Application No. PCT/GB2010/050531 dated Jun. 10, 2010.

* cited by examiner

METAL TREATMENT

The present invention relates to a method of treatment of a metal object to provide it with biocidal properties. In particular but not exclusively, the invention relates to treated metal objects that provide a reduced risk of irritation or infection when the object is in contact with a body.

Metal materials come into contact with the body in numerous situations, for example in surgery, where implants are used, these implants being inserted into the tissue of the body, be this soft or hard tissue. In the case of cancer treatment of the bone for example, cancerous bone tissue is removed, and a prosthetic metal implant is used to replace that part of the bone that has been removed. Implants are also used for partial or full replacement of bones in joints (e.g. hips) and also in other fields such as dentistry and maxillofacial surgery. Implants and medical devices may also be used in cases of amputation or trauma and such devices may be percutaneous of transcutaneous. Implants for the foregoing (and other) uses may be of titanium metal or titanium alloy. Titanium metal and titanium alloys are biocompatible, relatively strong and relatively light.

Further, metal comes into contact with the body in the case of jewellery. Much jewellery is made from metal alloys, but these may contain components that react with moisture in perspiration. Also, pitting of the metal alloy can occur due to the presence of chloride ions in the perspiration and this can create a seat for bacteria to accumulate which can then result in skin infections if the metal alloy comes into contact with broken skin. Irritation and infection can occur not only for jewellery that pierces the body but also for jewellery that sits next to the skin if the wearer has sensitive skin.

As can be seen, in both the medical and jewellery fields, the use of metal which comes into contact with body tissue runs the risk of introducing infection, or infection occurring. In both areas it has been suggested that metallic silver might be electroplated onto metal. Silver is known to have biocidal properties and the silver controls infection without causing toxic effects to the subject. However such coatings may be undercut due to corrosion from body fluids, so that the coating may detach from the metal, which may lead to increased wear and cause tissue damage from detached particles containing silver.

The present invention seeks to overcome the problems associated with the prior art by providing an anodised metal object having both hardwearing and biocidal properties, which can reduce the risk of infection. The invention can also be used in the prevention of biofilm formation. The invention has applications in a number of areas of technology, including medical fields, jewellery, and in other areas where a metal may come into contact with the body, for example when an individual is using a pen, handling cutlery or other domestic or industrial articles, or wearing spectacles, and this can have further applications to the healthcare industry where the risk of infection needs to be minimized. In effect the invention has applications in all areas where a metal article that has been anodised according to a method of the invention comes into contact with the skin, or body tissue; and in particular the invention is applicable to metal articles formed of metals such as titanium, or other valve metals such as niobium, tantalum or zirconium or their alloys, and also to those plated or coated with such metals or their alloys. The invention also has application to metal articles that have already been anodised for example by Type I, Type II or Type III anodising.

According to a first aspect of the invention, there is provided a method of treating a metal object so as to form thereon a surface layer which is integral with the metal object, and which includes a biocidal material, the method comprising:
(a) contacting the metal object, which is to provide a substrate for the surface layer, with an anodising electrolyte, and applying an anodising voltage to the metal object to passivate the metal by forming an anodised integral surface layer on the metal object;
(b) continuing the application of an anodising voltage to produce pits through the integral surface layer and into the substrate;
(c) producing a hydrous metal oxide in the surface layer by electrochemical or chemical reduction in contact with an electrolyte or a solution; and
(d) removing or separating the anodised metal object resulting from step (c) from the electrolyte or the solution of step (c); and
(e) contacting the anodised metal object with a solution containing a biocidal material so as to incorporate said biocidal material into the surface layer;
wherein the voltage in the pit-forming step (b) is less than the maximum voltage applied during the passivating step (a).

The reduction step, step (c), as a first option, comprises applying a negative voltage to the metal object that has been anodised during steps (a) and (b), while the metal object remains in contact with the anodising electrolyte. As a second option, the metal object that has been anodised during steps (a) and (b) may be put into contact with an electrolyte solution containing a reducible soluble salt of titanium or of the substrate metal, and subjected to a negative voltage to bring about electrochemical reduction. As a third option for step (c), instead of performing electrochemical reduction, the metal object may be contacted with a chemical reducing agent, after steps (a) and (b).

After anodisation in steps (a) and (b), it is believed that the solution contained within the surface pits contains a peroxy cationic complex of the substrate metal. This complex can be reduced electrochemically to a hydrous metal oxide of limited solubility, as in the first option for step (c) described above. This complex can similarly be reduced chemically, as in the third option for step (c). Rather than relying on this complex remaining in the pits, in the second option for step (c) an electrolyte solution is provided that contains a peroxy cationic complex, preferably a peroxytitanyl, which can be reduced electrochemically within the pits to hydrous titania.

Instead of using an external source of electricity for electrochemical reduction, the metal object may be made negative by connecting it electrically to an electrode of a corrodible metal, such as iron or steel; this may be immersed in the same electrolyte as the metal object, or in a separate electrolyte with ionic connection through a salt bridge or an ion-selective membrane. The corrodible metal electrode corrodes preferentially, so causing electrochemical reduction at the surface of the metal object.

In the case of chemical reduction (the third option for step (c)), where again a hydrous metal oxide is produced, the chemical reducing agent may be selected from one or more of the following: sodium sulphite, ferrous salts (chloride or sulphate), sodium nitrite, potassium bromide or iodide, or sodium borohydride or hydrazine. Stannous chlorides or sulphates, chromous chlorides or sulphates, or vanadous sulphates may be used under suitable conditions, although these have the disadvantage of polyvalent residues that may adsorb on the resulting hydrous titania.

Whichever option is selected for the reduction step, step (c), it results in the formation of hydrous metal oxides that have a high surface area. The high surface area allows for increased ion exchange with materials such as silver, which can be used as biocidal materials. Under some circumstances, depending on the electrolyte used, the hydrous metal oxide may be combined with a phosphate, and this has similar ion exchange properties.

The anodising is a two stage process with step (a) comprising the initial process of passivation i.e. growing a surface film of oxide, and then step (b) the formation of pits formed through said surface film into the substrate metal.

The maximum voltage applied during anodisation determines the thickness of the passive oxide film. Lower voltages applied subsequently do not affect the film thickness. The maximum voltage may be as high as 2000 V, but is more typically between 30 V and 150 V, for example 100V.

The voltage during passivation, step (a), may be applied as a voltage increasing linearly with time to a maximum, limiting value, or alternatively stepped voltages up to the maximum limit. It is also envisaged that multiple passivations may be used, where a voltage is applied repeatedly to prepare the metal surface for pitting. These different types of applying voltage all come within the definition of applying a voltage.

The voltage applied during step (b) is reduced to a lower value. Surprisingly, this has the effect of increasing both the rate and extent of pit development.

Preferably the applied voltage during the pit-forming step (b) is between 15 V and 80 V such as 20, 30, or 75 V. Desirably it is between 25 V and 60 V, for example 25 V or 30 V.

Preferably, in step (d), the metal object is rinsed to remove any electrolyte or solution remaining on the surface after the preceding steps. The rinsing may use water or any appropriate solvent. Then, in step (e), there is contact with the solution containing the biocidal material, which is preferably in the form of metal ions, to maximise the incorporation of the biocidal material in the surface layer on the metal object.

During the anodising procedure of steps (a) and (b), a positive voltage is applied to the metal. If step (c) uses electrochemical reduction then during step (c) a voltage is applied to the metal in the opposite sense i.e. is reversed, this being the negative voltage referred to herein in relation to step (c). The voltage reversal occurs after the end of step (b) that was used to create the pits. The pits constitute wells or reservoirs that are able to store the biocidal material. As a result of the anodising and subsequent steps, the metal object has a hard outer surface formed of an anodised layer, grown out from the surface (which can typically adsorb ~0.3-1.0 µg/cm$^2$ Ag), and through this layer or film are pits that can absorb additional ions of the biocidal material such as silver ions. The matrix contained within the pits receiving the biocidal material may be relatively soft and porous relative to the hard anodised surface, with greater ion exchange capacity, so that the metal object combines the properties of enhanced silver ion storage capacity with the harder anodised surface.

The biocidal material may comprise a biocidal metal and in particular, the biocidal metal may be or may comprise silver, although other metals may be used in addition to or as alternatives to silver, for example a combination of copper and silver. Preferably, the biocidal material (e.g. metal, such as silver) is provided in the solution of step (e) in the form of ions. It is envisaged that a colloidal type biocidal material may alternatively be used, for example a protein colloid might be adsorbed on the hydrous titania surface that could also release nutrients into a site in the body, which may assist in healing of the body where the implant is positioned.

The positive voltage in step (a) may be in the range 30 V up to 200 V but typically is in the range of 30 V to 150 V; it might be up to 750 V or 2000 V in an electrolyte with a high breakdown potential, such as lithium borate. Voltages that have been considered as useful are for example 35V, 100 V, 150 V or 200 V and these are particularly useful in the field of implants. After the growth of the passive layer (in step (a)) of desired thickness, hardness and colour, in step (b) pits may be grown in the surface in the same or a different electrolyte, at a lower potential, for example 2.1 M HPO$_4$ at 30 V as a separate step, followed by the reduction step to form hydrous titania in-situ (step (c)), rinsing (step (d)) and incorporation of biocidal material (step (e)).

The magnitude of the negative voltage during electrochemical reduction is preferably maintained or regulated so as to be insufficient to cause electrolysis of the solvent. The magnitude of the negative voltage affects the absorptive capacity of the surface, as it affects the magnitude of the reducing current; the electric charge passed is directly related to the creation of an adsorber matrix, and hence to the amount of biocidal material (e.g. metal, such as silver) which can subsequently be incorporated into the surface of the metal object. If the magnitude of the negative voltage is too low, the amount of biocidal metal subsequently incorporated may be insufficient to provide a desired level of biocidal properties; but carrying out the process for a longer time may compensate for the low voltage by increasing the reduction charge passed. The intention is to provide a negative voltage that produces the level of biocidal material in the treated object required to produce a biocidal/bacteriostatic effect, and which does so within a time frame that is commercially acceptable. It is possible to determine the magnitudes of negative voltage which do not cause electrolysis of the solvent while enabling desired amounts of biocidal metal to be subsequently incorporated into the surface of the metal object by monitoring the reduction current.

The negative voltage may be applied at least until the current through the metal object has caused the passage of sufficient charge to generate the desired adsorption capacity. Typically, the current drops during the application of the negative voltage, and the voltage is preferably applied until this current has fallen significantly, for example to less than 20% of the peak current. Typically this may take only 2 minutes. Indeed the current may drop to substantially zero. Typically, the initial value of the reduction current density is in the range of 0.05-2.0 mA/cm$^2$. The time over which the negative voltage is applied until the current falls to a suitably low value may be less than 300 s, and may be no more than 120 s. For example, in the case of a medical implant comprising titanium, if the molarity of the phosphoric acid is 2.1 M, the negative voltage may be in a range of from –0.2 to –0.7 V with respect to an Ag/AgCl standard reference electrode. This voltage range avoids electrolysis of the water solvent, which will occur at voltages below –0.7 V.

The metal of the metal object may comprise titanium or may comprise niobium, tantalum or zirconium, or an alloy comprising such a metal. The metal of the metal object may comprise other metals, for example the object might be of stainless steel plated or coated with a metal such as titanium or the other valve metals or their alloys. The invention also has application to metal articles that have already been anodised for example by Type I, Type II or Type III anodising. The metal of the metal object may be in the form of porous structures such as those manufactured using laser sintering. The invention is also applicable to sintered bead structures, and other porous forms of titanium or other valve metals.

The metal object can initially be polished to provide a very smooth surface. Titanium alloy can be electro-polished using acetic acid, or a mixture of nitric and hydrofluoric acids. Alternatively the material might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, acetic acid or sodium hydroxide mixed with sodium nitrate. Techniques such as grit blasting or shot blasting or shot peening may also be used to prepare the surface (e.g. for subsequent application of hydroxyapatite by plasma spraying after biocidal ion loading, to stimulate localised bone attachment). Also, the surface may be spray coated with titanium to provide a rough surface.

After polishing or other treatment of the surface of the metal object, surface modification or conversion can take place as described above. A layer of a metal oxide material which may include some phosphate (for example when using phosphoric acid electrolyte) is formed by anodising and then reducing in a suitable electrolyte. Biocidal metal species, e.g. ions, can then be absorbed or adsorbed into the oxide and/or phosphate layer in a subsequent step by treating the anodised metal surface with the solution containing biocidal material. The biocidal metal species in the solution may be in the form of ions, for example silver ions (or $Cu^{++}$), and these ions are then absorbed/adsorbed by ion exchange into the oxide and/or phosphate layer. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate layer, this reaction being performed chemically or electrochemically or by light.

The anodising electrolyte preferably comprises phosphoric acid as a dilute solution of a desired pH in a solvent. The solvent may comprise water. Other electrolytes such as sulphuric acid, phosphate salt solutions or acetic acid may be used. Alkaline electrolytes such as sodium hydroxide may be used also. It is preferred that these electrolytes are in a diluted form for example 2.1 M $H_3PO_4$, or 0.1 M $H_2SO_4$.

Gentle agitation may be desirable during the passivation step (a) when high currents flow, in order to minimise local heating effects. This is beneficial in improving process uniformity over a single item, and also over a group of units being treated simultaneously. Preferably, movement or circulation of the electrolyte relative to the surface of the metal object is suppressed or inhibited during step (b) when microscopic pits are being formed through the said surface layer (b). So during the pit growth step (b), it is preferred that no stirring of the electrolyte should be performed, and/or means such as baffles, or additives such as gelling agents to increase the viscosity of the electrolyte may be used to prevent or reduce electrolyte movement. It has been found that increased levels of hydrous metal oxide (e.g. hydrous titanium oxide) are subsequently formed if the electrolyte is not moved or circulated relative to the surface of the metal object during step (b), and that higher levels of biocidal metal can be incorporated into the resulting anodised surface, without giving rise to toxic effects when the metal object is used.

The phosphoric acid may have a concentration in a range of from 0.01 M to 5.0 M, typically from 0.1 M to 3.0 M and in particular 2.0 M. Preferably, the pH of the acidic electrolyte should be maintained within the range of 0.5<pH<2.0—more ideally within the range 0.75<pH<1.75.

If an alkaline electrolyte is used the pH is preferably greater than 9 and more typically the pH is in the range of 10-14. The alkaline electrolyte can be a phosphate salt such as $Na_3PO_4$, or may be sodium hydroxide, NaOH.

In instances where other metal substrates or anodising electrolytes are used instead of phosphoric acid, sulphuric acid or acetic acid, the magnitude of the negative (i.e. reverse) voltage may need to be adjusted to provide the desired effects due to factors such as changes in pH, or even temperature.

The geometric surface area of the metal object can be determined by conventional means such as the use of standard measuring devices such as callipers, micrometers and rulers combined with a geometric model of the item being treated e.g. using Computer Aided Design (CAD), or more advanced optical methods such as laser scanning. This measurement does not however take into account microscopic surface features or surface roughness of the metal. This microscopic surface area is an important factor in determining and controlling how much charge is passed during the anodisation step. The microscopic surface area can be determined, for example, by immersion of the metal object (such as an orthopaedic implant) in an electrolyte, and measuring the double layer capacitance and comparing this to calibrated standards under identical conditions of temperature and electrolyte concentration. The charge or current per microscopic surface area e.g. $coulomb/cm^2$ or $mA/cm^2$ is therefore typically used in the control of the anodising process. The ratio of microscopic to geometric area is known as the surface roughness factor and can be used to convert one area to the other. For example, a 10 $\mu g/cm^2$ silver loading on a geometric area basis would correspond to a 5 $\mu g/cm^2$ silver loading on a microscopic area basis for a roughness factor of 2. The silver loading per geometric area is the parameter typically used for describing an orthopaedic implant.

During the passivation step (a), the current may be controlled, or alternatively the voltage may be controlled. The anodising may be performed with a maximum current density in a range of from 0.1 to 100 $mA/cm^2$, preferably 0.1 to 50 $mA/cm^2$, or more typically 1 to 10 $mA/cm^2$, e.g. 5 $mA/cm^2$ or thereabouts. Alternatively, an applied voltage linearly increasing with time, preferably at between 0.1 V/s and 10 V/s, for example at 1 V/s or 0.5 V/s, or increasing in steps, may be applied to control the passivation process. In either case the applied potential is raised to a maximum value (e.g. of 100 V). When the desired maximum voltage has been reached, the voltage is held constant, and as the passivation reaches completion the current falls to a significantly lower value.

The passivation step (a) may be considered to be complete when the current has decreased to a low value. In accordance with the present invention the applied voltage is then decreased to a lower value to perform the pit-forming step (b). Surprisingly, by operating at a lower voltage, the electric current is considerably higher, and the time taken to produce the pits is consequently considerably reduced.

The present invention also provides methods of treating a metal object as specified in one or more of the claims following this description.

According to a further aspect of the invention, there is provided a metal object obtained by the methods described above and hereinafter.

The metal object may be in the form of an implant, a medical implement or device or jewellery. In particular, in the case of a medical implement or device, this could include any type of device or tool that comes into contact with the body, for example pace-makers, stents, skin staples, scalpels, trocars, pins for bones or even medical implements such as scalpels or tissue clamps which are used during surgery.

The metal object has desirable biocidal properties to suppress and/or control infection without toxic effects on an individual, whether animal or human, that comes into contact with the material.

Implants according to the invention can be used for many medical and surgical purposes, including full and partial hip replacements, implants useful in maxillofacial, trauma, urology, orthodontal and orthopaedic applications, arthroscopic devices, dental implants, neurological apparatus and parts (such as staples, nails and pins) used in cardiovascular and general surgery.

The jewellery that can be made from the metal object according to the invention can include all types of jewellery. The jewellery can be conventional jewellery such as rings, necklaces and bracelets or the jewellery can be of the type that is held within an aperture in the body, for example jewellery that pierces the body e.g. earrings, navel rings, rings to be inserted through other fleshy parts of the body such as the lips, cheeks etc.

The metals that may be used to make the implants or jewellery according to the invention may be titanium or a titanium alloy. One standard alloy for this purpose is titanium 90% with 6% aluminium and 4% vanadium (British Standard 7252). Alternatively the metal may comprise niobium, tantalum or zirconium, or alloys of these metals.

For an implant or jewellery for piercing the body, it may be desirable that the surface of the material is highly polished before production of the surface layer by anodising. In the case of implants, a highly polished surface reduces any tendency for local calcification when the implant comes into contact with bone. A polished surface also permits smooth movement of muscle and tissue over the surface with minimal fretting or wear. Suitable polishing may be attained by known techniques, such as (e.g.) mechanical polishing and/or electropolishing.

The invention will now be further and more particularly described, by way of example only, with reference to the accompanying figures, in which.

The process will now be described in relation to the treatment of a metal implant for use in a surgical procedure. The implant is first cleaned, by an aqueous or non-aqueous process (unless it had been sufficiently cleaned during manufacture). The cleaning process may be by ultrasonic cleaning using first acetone as the liquid phase (or other degreasing solvent), then rinsed with fresh acetone (or other solvent) and then with de-ionized water or any other suitable rinsing solution. The metal implant may then be cleaned in a 1 M aqueous solution of sodium hydroxide (or other alkaline cleaner) and then rinsed in de-ionized water. The resulting cleaned metal implant is then anodised in contact with an aqueous solution of phosphoric acid, which in this example is 2.1 M, as the anodising electrolyte. The implant, in this example, is anodised using a maximum voltage of 100 V, to produce a hard wearing anodised oxide surface layer.

Figure 1:
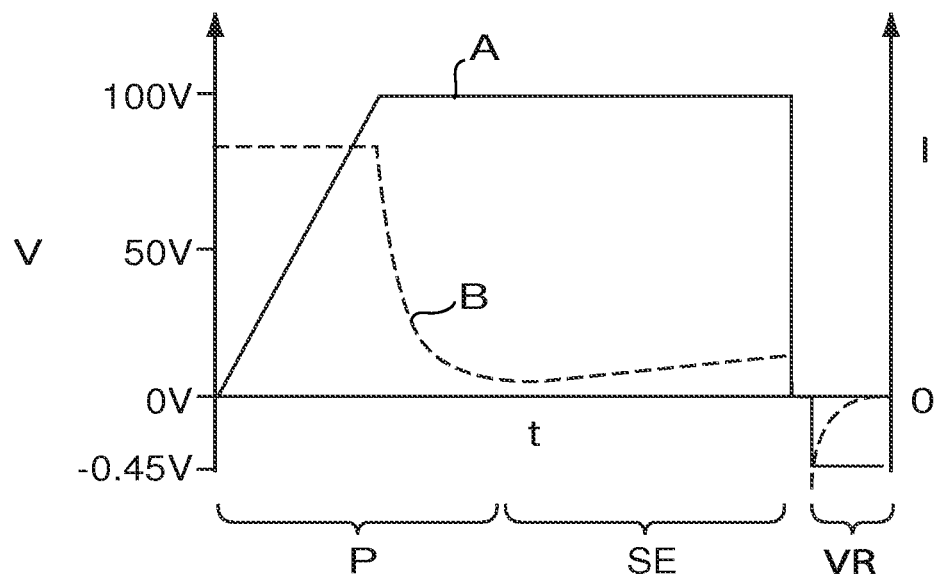
FIG. 1 shows a diagrammatic representation of the voltages and currents used during surface treatment.
Figure 2:
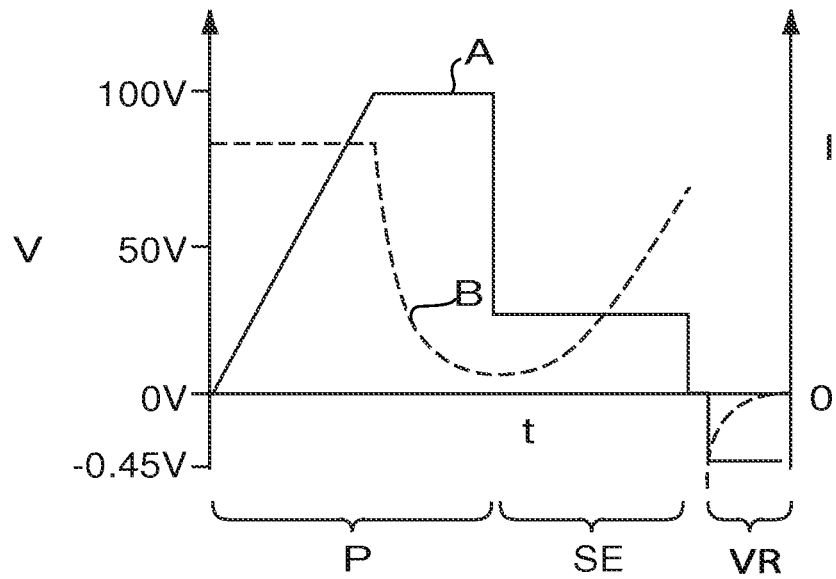
FIG. 2 shows a diagrammatic representation of the voltages and currents used during surface treatment according to an embodiment of the invention.

FIGS. 1 and 2 show schematic graphs of current and voltage levels used in the anodizing of a titanium metal object such as a medical implant or an item of jewellery. The treatment process illustrated in FIG. 1 is substantially that described in WO 2009/044203 (Accentus). In each case the voltage is shown as an unbroken line (A) and the current as a broken line (B). The graph shows current (I) and voltage (V) applied over time (t); the graphs are a schematic representation and not to scale. During the initial application of voltage the potential is, in this example, controlled using a current limiter which could be in the range of 2.5-10 mA/cm$^2$ but other levels can be used. A preferred current intensity limit for treating titanium alloy is 5 mA/cm$^2$, whereas with pure titanium the preferred limit is in the range 7.5-25 mA/cm$^2$, or more particularly 7.5-10 mA/cm$^2$. The anodising current results in formation of an oxide layer that is integral with the titanium metal substrate, passivating the surface. During the current-limited period the applied potential supplied from the power supply gradually increases as the thickness of the oxide film grows. The voltage is increased to a predetermined limit, which is selected according to the properties required for the surface layer. When the voltage limit is reached, 100 V in this example, the voltage is then held at that level, and the current falls to a low level, for example less than 1 mA/cm$^2$ and this drop in current indicates that passivation (marked as P) has been completed.

The passivating process forms a hard surface that can have different coloured appearances due to optical interference effects. During the initial steps of anodising, the surface colour varies from gold to purple, blue, through to colourless, green, yellow, orange and finally red/purple. Anodising at 100 V produces a film thickness of about 140 nm, and a purple colour, the film being hard wearing. The oxide thickness is approximately 1.4 nm/V, the maximum voltage determining the thickness of the hard oxide layer, which in turn influences the colour formed. For example in 2.1 M phosphoric acid, a maximum voltage of about 30 V will produce a layer of thickness about 42 nm with a blue colour. The provision of different colours may be desirable for aesthetic reasons, or to enable different types of articles (such as implants) to be readily distinguished.

Once passivation (P) has been completed, an anodising voltage is maintained to allow for surface engineering (shown as SE) of the passivated metal surface, as pits are formed in the surface. The voltage level and the time selected for applying the voltage can be chosen according to the coverage and dimensions of the pits required for the surface.

The surface of the thus-anodised implant based on titanium comprises a hard surface layer comprising a titanium oxide, in which are pits or pitted regions. The pits and/or pitted regions are believed to contain titanium oxide and might also contain a soluble titanium compound. The pits typically have depths in the range 1 to 3 μm penetrating through the outer passive hard oxide layer (which is 0.14 μm thick at 100 V) into the substrate, and have typical diameters of 1 to 5 μm. The pits may occupy some 5 to 20% of the surface area, though preferably below 10%, so they do not significantly affect the hard wearing properties of the hard surface layer. However, by using lower voltages during step (b), as shown in FIG. 2, higher silver loading can be achieved—with pit densities up to 50%.

Once the passivation and the production of pits to a required format are complete, the metal object is subjected to a voltage reversal (shown as VR) which results in an observed negative current. During treatment with (e.g.) a 2.1 M aqueous phosphoric acid solution, the reversed voltage is applied with a voltage in the range of from −0.2 to −0.7 V, e.g. −0.3 to −0.6 V, more specifically—0.40 to −0.55 V, and exemplified by about −0.45 V (as measured with respect to a Ag/AgCl standard reference electrode), to ensure that the solvent, water, is not electrolysed, but that a reduction process is able to take place. It is believed that during the period of reversed voltage, VR, certain titanium species are electrochemically reduced within the pits to high surface area, low solubility, hydrous titanium oxide species, and so the pits fill with this high surface area inorganic medium. As the reversed voltage is applied, the current through the implant drops from an initial value, and eventually falls to zero or substantially zero. It is believed that the fall in current is due to the depletion of the reducible titanium species as it forms the low-solubility hydrous titania species in the pits. Substantially complete reduction to the hydrous titania is typically attained after a cathodic charge in the range of from 0.005 to 0.2 coulomb/$cm^2$, e.g. in the range of from 0.01 to 0.05 coulomb/$cm^2$. When the reversed current has fallen sufficiently, e.g. to less than 20% of the initial value, preferably to zero or thereabouts, the reversed potential is stopped. The reversed voltage step, VR, may take from 60 to 180 s.

It is thought that during anodisation, during step SE, peroxytitanyl ($TiO_2^{2+}$) is generated locally (as the phosphate salt) through titanium dissolution under the anodic conditions in the pits. On subsequent voltage reversal, this will be reduced to $Ti(OH)_4$ (hydrous titania), which is essentially insoluble in the electrolyte above a pH of around 0.5, and so this material is retained in the pit/pore as a solid. The hydrous titania is an inorganic ion-exchange medium that can become saturated with cations such as silver cations when subsequently contacted with silver nitrate, $AgNO_3$, solution.

It is also possible for the voltage reversal step, VR, to use as an electrolyte a solution containing dissolved peroxytitanyl salts synthesised chemically (e.g by dissolving $Ti(OH)_4$ in an acidic electrolyte solution containing hydrogen peroxide). (An equivalent process can be carried out using an alkaline electrolyte.) No reduction reaction will take place at the passivated surface of the anodised item due to the semiconductor properties of the oxide film, but electroreduction occurs locally within the pits. For metal substrates—especially those of non-titanium based materials e.g. Nb, Ta, Zr and their alloys—this may be a useful method of introducing the hydrous titania adsorber medium into the surface, prior to subsequent biocide adsorption. The adsorber might instead be based on the metal from which the implant is to be made, for example, niobium or zirconium, but for cost effectiveness, titania is preferably used.

When the anodising steps, P and SE, and reduction step, VR, have been completed, the surface of the anodised implant is rinsed with de-ionised water to remove phosphoric acid residues and other soluble materials. The thus-cleaned implant is next immersed in a solution comprising the biocidal material, which is silver in this example, typically for between 0.5 hours and 2 hours, for example 1 hour. The solution is an aqueous solution of silver nitrate having a silver concentration in the range of from 0.001 to 10 M, e.g. 0.01 to 1.0 M, for example, 0.1 M or thereabouts. Silver ions are absorbed within the surface, presumably by ion exchange, the greatest concentration being in the material within the pits.

The treated implant may have a silver content of 0.5 to 40 $\mu g/cm^2$ or more typically from 2-20 $\mu g/cm^2$. The silver is present initially mainly in ionic form but may be at least partially converted to atomic clusters of metal dispersed within the hydrous titania adsorption matrix as a result of photo-reduction. Typically, ~0.3-1 $\mu g/cm^2$ is adsorbed on the hard passive layer, with the remainder stored within the hydrous titania-filled pits.

Referring again to the anodising steps P and SE, the desired degree of anodising is usually obtained after a charge of from 2 to 5 coulombs/$cm^2$ of surface area of the implant has been passed. A suitable charge would be about 3.5 coulombs/$cm^2$. If, as shown in FIG. 1, the anodising voltage is maintained at its maximum value (100 V in this example) during the surface engineering step, SE, the anodising process typically takes 2 to 4 hours.

Referring now to FIG. 2, the process of the present invention is as described above, with the exception that the surface engineering step SE, that is to say the step during which the pits are formed, is carried out at a significantly lower voltage. As shown in FIG. 2, when passivation has been achieved—end of stage P being indicated by a low current value—the voltage is then reduced to 20-80 V, for example 30, 35 or 75V. This has a surprising effect: the current is significantly larger than is observed when maintaining the voltage at 100 V. A result of this is that the same degree of pit formation can be achieved much more rapidly, and that a greater degree of pit formation can be achieved in considerably less time than is required at 100V. The subsequent loading of silver in the treated item is directly related to the degree of pit formation, and so can be similarly enhanced.

For example, the passivation step P may take between 1 and 10 minutes. The passivation step P may be ended, and the step SE started, on the basis of observations of the current, for example when the current or the current density falls below a threshold, or when the rate of decrease of current falls below a threshold. If the voltage is maintained at 100 V during the pit-formation step SE (as in FIG. 1) so that the total duration of the process is 3 hours, then the silver loading can be 3.0 $\mu g/cm^2$, on a microscopic basis, or between 4.5 and 5.5 $\mu g/cm^2$ on a geometric basis. In contrast, a silver loading of 4.0 $\mu g/cm^2$ on a microscopic basis and between 5.0 and 6.0 $\mu g/cm^2$ on a geometric basis can be achieved by holding the voltage during the pit-formation step SE (as in FIG. 2) at 20 V for 13 min. Thus the total treatment time is very considerably decreased.

Furthermore, the longer the period at which the voltage is held at the lower value, then the greater is the degree of formation of pits, and the greater the resultant silver loading in the treated product. For example 20V for 26 min would approximately double the silver loading. It will be appreciated that there is a limit to the degree of pit formation that is acceptable, if the wear resistance of the hard anodised oxide layer is to be maintained.

Experimental measurements have been carried out to investigate how the final silver loading is affected by the voltage applied during the pit-formation step SE. Nine different titanium samples were passivated (P), raising the voltage at 0.5 V/s to a maximum of 100 V, and then maintaining the potential at 100 V for 10 minutes. The samples were then subjected to pit-formation SE for a further 20 minutes at a range of different voltages from 15 V up to 100 V. Each sample was then subjected to voltage reversal, VR, for about 2 minutes. And then, after rinsing, each was subjected to ion exchange with silver nitrate solution for 1 hour. By way of comparison, a tenth sample was treated as shown in FIG. 1, performing pit-formation SE at 100 V but continuing for a total anodising time of 3 hours, before performing ion exchange in the same way.

Figure 3:
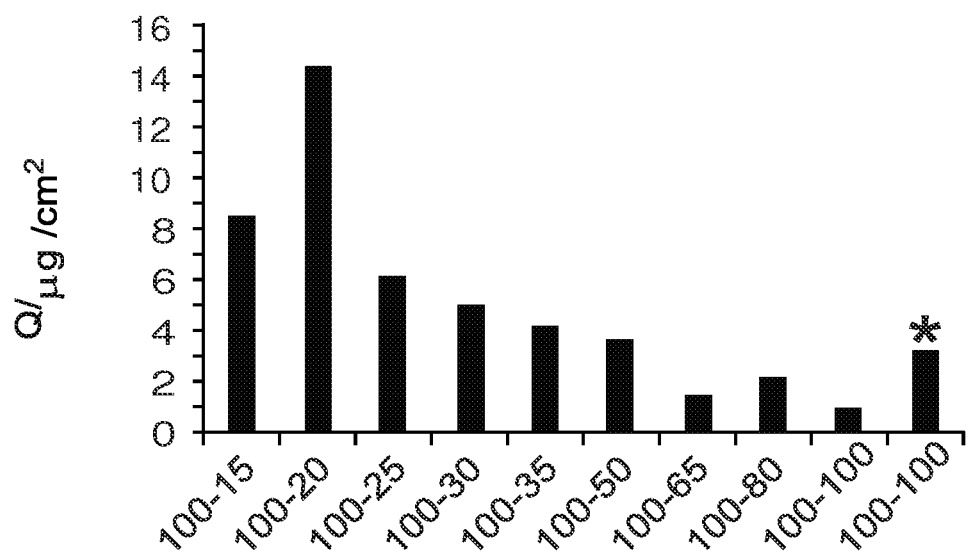
FIG. 3 shows graphically the silver loading achieved by a range of different surface treatments.

The silver loadings, Q, on a geometric basis, of the samples was as shown in the table and as shown graphically in FIG. 3. The comparative sample, treated as in FIG. 1, is shown in the last row and marked with an asterisk. The table also shows the total time taken for the anodising (i.e. P and SE).

TABLE

| SE voltage | Anodising Time/min | Q/$\mu g/cm^2$ |
|---|---|---|
| 15 | 30 | 8.56 |
| 20 | 30 | 14.52 |
| 25 | 30 | 6.24 |
| 30 | 30 | 4.96 |
| 35 | 30 | 4.24 |
| 50 | 30 | 3.70 |

TABLE-continued

| SE voltage | Anodising Time/min | Q/µg/cm² |
|---|---|---|
| 65 | 30 | 1.49 |
| 80 | 30 | 2.18 |
| 100 | 30 | 1.00 |
| 100 | 180 | 3.38* |

The measurements of silver loading, Q, are accurate to +/−20%, and in each case there was only a single sample. Nevertheless the measurements show very clear trends. Reducing the voltage during the pit formation stage SE to below 65 V enables equivalent or better silver loading to be achieved in only 30 min, as compared to maintaining the voltage at 100 V for an anodising period of 3 hours. And reducing the voltage during the pit formation stage SE leads to increased silver loading as compared to maintaining the voltage, if the times are equal.

The silver loading was found to increase as the SE voltage decreased, and to be greatest when the SE voltage was at 15 or 20 V. However it was also observed that the resulting surface finish was less satisfactory, as the pits tended to be clustered together, and the oxide surface was partly friable. On the other hand at SE voltages above about 25 V the pits were well distributed over the surface, and the surface had good integrity.

The optimum treatment will depend upon the required properties of the metal object. For example where the object is required to have high silver levels, but where surface appearance is not of concern or where the object is not required to be hard wearing, then it may be acceptable to perform the pit formation step SE at as low as 15 V or 20 V. The friable surface finish may be reduced by decreasing the time taken for pit formation SE, for example to 10 minutes; or it may be reduced by performing the passivation at a higher voltage.

In contrast, where the object is required to have an attractive surface appearance, or to be hard wearing, while still having adequate biocidal properties, then it would be desirable to perform the pit formation step SE at a voltage above 20 V. The SE voltage is preferably between 25 V and 60 V, more preferably between 25 V and 50 V, such as 30 V, as this provides good silver loading while maintaining a good quality surface finish and integrity. At significantly higher voltages, for example above 90 V, the benefits of the present invention are not obtained, The way in which the passivation step P is carried out also affects the degree of pit formation, and so the silver loading. As described above the initial increasing voltage may be applied under current control. Typically this is observed to give a rate of increase of voltage of about 2.5 V/s. Alternatively, as in the examples described above, the potential may be increased linearly with time up to the maximum value. As a general rule, the slower the passivation voltage increases, the higher is the final silver loading, correlating with an increase in pit density. This suggests that the pits are initiated during the passivation stage P, and then grow during the pit-formation stage SE.

The voltage during passivation, P, may be increased linearly, or there may be steps of voltage, for example of 2 V, 5 V or 10 V. As another example the voltage might initially be raised to say 5 V, held for a few minutes, for example 5 minutes, and then raised again either step-wise or linearly to the maximum voltage (e.g. 100 V).

As another example, Ti6Al4V alloy discs were cleaned and then anodised in 2.1 M $H_3PO_4$ at 20° C. increasing the voltage to 15 V at 0.5 V/s; then restarting and raising the voltage to 100 V at 0.5 V/s; holding the voltage at 100 V for 10 minutes, and then dropping the voltage to 20 V and holding for 20 minutes. This differs from the process described above by the initial 15 V anodising step. The discs were then subjected to reduction: one disc was subjected to electrochemical reduction as described above; one disc was connected to a mild steel electrode immersed in the electrolyte for 4 minutes (equivalent to −0.66 V AgCl/Ag); and another disc was reduced chemically using sodium nitrite solution. All the discs were then rinsed with deionised water before immersion in stirred 0.1 M $AgNO_3$ for 1 hour. The resultant silver loadings, Q, on a geometric basis, for these three discs were as follows: electrochemical, 4.41 µg/cm²; steel electrode, 5.72 µg/cm²; and sodium nitrite, 7.05 µg/cm².

In use of the treated metal object it is thought that during exposure to body fluids there is a slow leaching of silver species from the anodised layer, so that the growth of microorganisms such as bacteria, yeasts or fungi in the vicinity of the metal object is inhibited. The leaching is thought to be effected by ion exchange of silver on the metal object with sodium in the body fluids that contact the metal object. Other mechanisms such as the oxidation of the metallic silver to ionic species by means of the localised oxygen levels can occur to produce the released silver ions which can go on to kill or suppress the growth of the microorganisms or biofilm formation.

It is to be understood that references herein to silver as a biocidal metal also apply to other biocidal metals, such as copper, gold, platinum, palladium or mixtures thereof, either alone or in combination with other biocidal metal(s).

It is also envisaged that a bone promoting material such as hydroxyapatite may be coated on the metal implant once the biocidal material has been introduced.

Although individual embodiments of the invention are discussed, it is to be understood that combinations of the individual embodiments fall within the scope of the invention as claimed and described.

What is claimed:

1. A method of treating a metal object so as to form thereon a surface layer which is integral with the metal object, and which includes a biocidal metal, the method comprising:
   (a) contacting the metal object, which is to provide a substrate for the surface layer, with an anodising electrolyte comprising phosphoric acid, and applying an anodising voltage of between 30 V and 150 V to the metal object to passivate the metal by forming an anodised integral surface layer on the metal object, wherein the metal object comprises titanium, niobium, tantalum or zirconium, or an alloy comprising such a metal;
   (b) continuing, in the same electrolyte, the application of an anodising voltage to produce pits through the integral surface layer and into the substrate;
   (c) producing a hydrous metal oxide in the surface layer by electrochemical reduction in contact with an electrolyte or a solution;
   (d) removing or separating the anodised metal object resulting from the electrochemical reduction of step (c) from the electrolyte or the solution of step (c); and
   (e) contacting the anodised metal object with a solution containing a biocidal metal so as to incorporate said biocidal metal by ion exchange into the surface layer;
   wherein the voltage in the pit-forming step (b) is less than the maximum voltage applied during the passivating step (a) and is between 20 V and 60 V; and wherein the anodising steps (a) and (b) are performed in a total time of no more than 60 minutes.

2. The method of claim 1, wherein the voltage applied in the passivating step (a) is increased at no more than 5 V/s.

3. The method of claim 1, wherein the voltage applied in the passivating step (a) is increased stepwise.

4. The method of claim 1, wherein in passivating step (a) the voltage is maintained at a value below 50 V for a period between 1 and 20 minutes, prior to raising to the maximum voltage.

5. The method of claim 4, wherein the voltage is maintained at a value between 3 and 35 V for a period between 2 and 5 minutes, prior to raising to the maximum voltage.

6. The method of claim 1, wherein in passivating step (a) the voltage is raised to a value below 50 V, and then dropped to zero, before raising to the maximum voltage.

7. The method of claim 1, wherein the amount of charge employed for anodising in steps (a) and (b) is in the range from 0.5 to 10 coulomb/cm$^2$.

8. The method of claim 1, comprising multiple passivation steps (a).

9. The method of claim 1, wherein the hydrous metal oxide is produced in step (c) by application of a negative voltage to the metal object, and the negative voltage is applied for less than 300 seconds.

10. The method of claim 1, wherein the anodizing electrolyte is agitated during the passivating step (a), and/or movement of the electrolyte relative to the surface of the metal object is inhibited during the pit-producing step (b).

11. The method of claim 1, wherein the voltage in the pit-forming step (b) is 30 V.

12. The method of claim 1, wherein the voltage in the pit-forming step (b) is between 25 V and 50 V.

* * * * *